United States Patent
Uchida et al.

(10) Patent No.: US 11,450,135 B2
(45) Date of Patent: Sep. 20, 2022

(54) FINGERPRINT DETECTION APPARATUS AND DISPLAY APPARATUS

(71) Applicant: Japan Display Inc., Tokyo (JP)

(72) Inventors: Makoto Uchida, Tokyo (JP); Takanori Tsunashima, Tokyo (JP); Masahiro Tada, Tokyo (JP); Tomoyuki Ito, Tokyo (JP); Takashi Nakamura, Tokyo (JP)

(73) Assignee: Japan Display Inc., Tokyo (JP)

( * ) Notice: Subject to any disclaimer, the term of this patent is extended or adjusted under 35 U.S.C. 154(b) by 0 days.

(21) Appl. No.: 17/033,040

(22) Filed: Sep. 25, 2020

(65) Prior Publication Data

US 2021/0012082 A1    Jan. 14, 2021

Related U.S. Application Data

(63) Continuation of application No. PCT/JP2019/005165, filed on Feb. 13, 2019.

(30) Foreign Application Priority Data

Mar. 27, 2018 (JP) .............................. JP2018-060124

(51) Int. Cl.
    *G06V 40/13* (2022.01)
    *H01L 27/146* (2006.01)
    *G06F 3/044* (2006.01)
(52) U.S. Cl.
    CPC .... *G06V 40/1318* (2022.01); *H01L 27/14678* (2013.01); *G06F 3/044* (2013.01)
(58) Field of Classification Search
    None
    See application file for complete search history.

(56) References Cited

U.S. PATENT DOCUMENTS

| 5,598,004 A | 1/1997 | Powell et al. |
| 2003/0010922 A1 | 1/2003 | Yoon et al. |

(Continued)

FOREIGN PATENT DOCUMENTS

| JP | H09503351 A | 3/1997 |
| JP | 2000340777 A | 12/2000 |

(Continued)

OTHER PUBLICATIONS

International Search Report issued in Application No. PCT/JP2019/005165, dated Apr. 23, 2019.

*Primary Examiner* — Joseph R Haley
(74) *Attorney, Agent, or Firm* — K&L Gates LLP

(57) ABSTRACT

A fingerprint detection apparatus comprising: an insulating substrate; a plurality of photoelectric conversion elements arrayed in a detection region of the insulating substrate, each of the photoelectric conversion elements configured to output a signal in accordance with light incident on each of the photoelectric conversion elements; first switching element, each corresponding to each of the photoelectric conversion elements and including a first semiconductor made of oxide semiconductor; a plurality of gate lines coupled with the first switching elements and extending in a first direction; a plurality of signal lines coupled with the first switching elements and extending in a second direction intersecting the first direction; and a gate line drive circuit including a second switching element that includes a second semiconductor made of polycrystalline silicone, the gate line drive circuit being provided in a peripheral region outside the detection region and configured to drive the gate lines.

20 Claims, 11 Drawing Sheets

(56) References Cited

U.S. PATENT DOCUMENTS

| | | | |
|---|---|---|---|
| 2007/0045556 A1 | 3/2007 | Watanabe et al. | |
| 2008/0210946 A1 | 9/2008 | Okada et al. | |
| 2009/0032680 A1 | 2/2009 | Watanabe et al. | |
| 2015/0255017 A1* | 9/2015 | Kim | G09G 3/3225 315/172 |
| 2016/0041274 A1 | 2/2016 | Park et al. | |
| 2016/0190202 A1 | 6/2016 | Fujiwara et al. | |
| 2016/0366360 A1 | 12/2016 | Okamoto et al. | |
| 2017/0256207 A1* | 9/2017 | Takahashi | G09G 3/3233 |
| 2017/0262121 A1* | 9/2017 | Kurasawa | G06F 3/0443 |
| 2017/0357011 A1 | 12/2017 | Tomiyasu et al. | |
| 2018/0012069 A1 | 1/2018 | Chung et al. | |
| 2019/0088184 A1* | 3/2019 | Morein | G06F 3/0412 |
| 2019/0239808 A1* | 8/2019 | Lim | A61B 5/1128 |

FOREIGN PATENT DOCUMENTS

| | | |
|---|---|---|
| JP | 2004087604 A | 3/2004 |
| JP | 2005276030 A | 10/2005 |
| JP | 2005311487 A | 11/2005 |
| JP | 2007059887 A | 3/2007 |
| JP | 2007096282 A | 4/2007 |
| JP | 2008177556 A | 7/2008 |
| JP | 2017005713 A | 1/2017 |
| WO | 2015019609 A1 | 2/2015 |
| WO | 2016111192 A1 | 7/2016 |

* cited by examiner

FINGERPRINT DETECTION APPARATUS AND DISPLAY APPARATUS

CROSS-REFERENCE TO RELATED APPLICATION

This application is a continuation of PCT international application Ser. No. PCT/JP2019/005165 filed on Feb. 13, 2019 which designates the United States, incorporated herein by reference, and which claims the benefit of priority from Japanese Patent Application No. 2018-060124, filed on Mar. 27, 2018, incorporated herein by reference.

BACKGROUND

1. Technical Field

The present disclosure relates to a fingerprint detection apparatus and a display apparatus.

2. Description of the Related Art

Recently, an optical fingerprint sensor has been known as a fingerprint sensor used for personal authentication or the like (for example, U.S. Patent application publication No. 2018/0012069). The optical fingerprint sensor includes a photoelectric conversion element, an output signal from which changes in accordance with the quantity of incident light. In a fingerprint sensor disclosed in U.S. Patent application publication No. 2018/0012069, a plurality of photoelectric conversion elements such as photodiodes are arrayed on a semiconductor substrate.

It is potentially difficult to increase the area of a detection region in which a fingerprint is detected in a fingerprint sensor including a semiconductor substrate. Furthermore, the size of a drive circuit configured to drive the fingerprint sensor increases as the area of the detection region increases. Thus, the manufacturing cost of the fingerprint sensor potentially increases.

SUMMARY

A fingerprint detection apparatus according to one embodiment of the present disclosure includes an insulating substrate, a plurality of photoelectric conversion elements arrayed in a detection region of the insulating substrate, each of the photoelectric conversion elements configured to output a signal in accordance with light incident on each of the photoelectric conversion elements, first switching elements, each corresponding to each of the photoelectric conversion elements and including a first semiconductor made of oxide semiconductor, a plurality of gate lines coupled with the first switching elements and extending in a first direction, a plurality of signal lines coupled with the first switching elements and extending in a second direction intersecting the first direction, and a gate line drive circuit including a second switching element that includes a second semiconductor made of polycrystalline silicone, the gate line drive circuit being provided in a peripheral region outside the detection region and configured to drive the gate lines.

A display apparatus according to one embodiment of the present disclosure includes, the fingerprint detection apparatus described above, and a display panel including a display element for displaying an image and disposed opposite to the fingerprint detection apparatus.

DETAILED DESCRIPTION

Modes (embodiments) for carrying out the present disclosure will be described below in detail with reference to the accompanying drawings. The present disclosure is not limited by the contents of the following description of the embodiments. Components described below include those easily thought of by the skilled person in the art and those identical in effect. Moreover, configurations described below may be combined as appropriate. The disclosure is merely exemplary, and any modification that can be easily thought of by the skilled person in the art as appropriate without departing from the gist of the invention is included in the scope of the present disclosure. For further clarity of description, each drawing schematically illustrates the width, thickness, shape, and the like of each component as compared to those in the actual configuration in some cases, but the illustration is merely exemplary and does not limit interpretation of the present disclosure. In the present specification and the drawings, any element similar to that described with reference to a drawing already described is denoted by an identical reference sign, and detailed description thereof is omitted as appropriate in some cases.

First Embodiment

Figure 1:
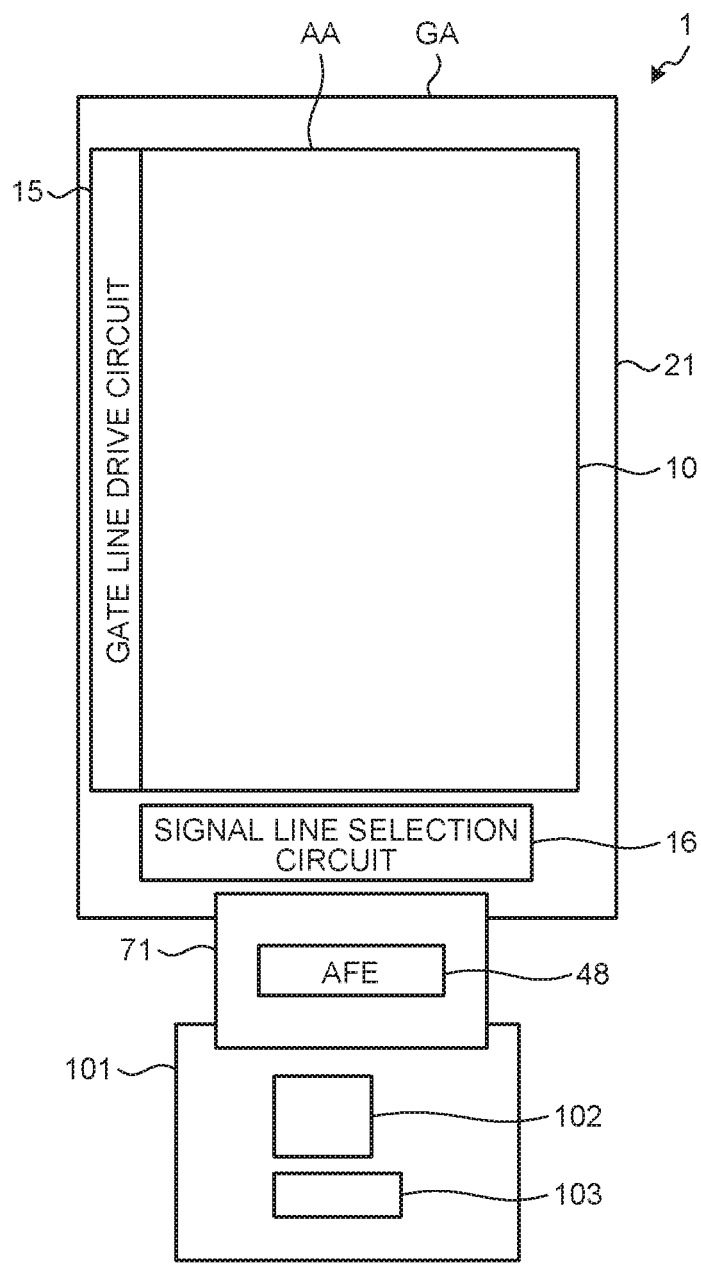
FIG. 1 is a plan view illustrating a fingerprint detection apparatus according to a first embodiment.
Figure 2:
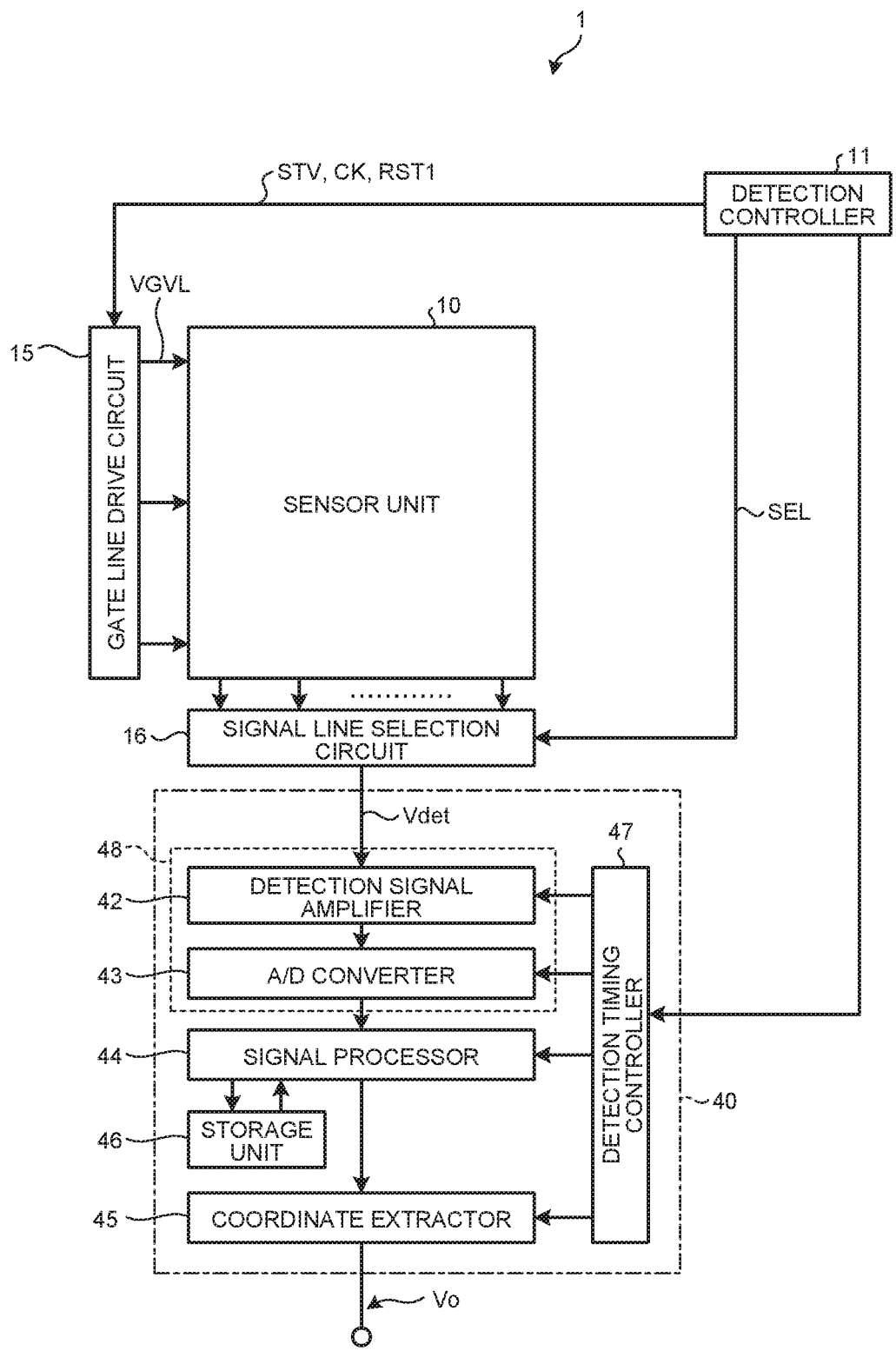
FIG. 2 is a block diagram illustrating an exemplary configuration of the fingerprint detection apparatus according to the first embodiment.

FIG. 1 is a plan view illustrating a fingerprint detection apparatus according to a first embodiment. FIG. 2 is a block diagram illustrating an exemplary configuration of the fingerprint detection apparatus according to the first embodiment. As illustrated in FIG. 1, this fingerprint detection apparatus 1 includes an insulating substrate 21, a sensor unit 10, a gate line drive circuit 15, a signal line selection circuit 16, an analog front-end circuit (hereinafter referred to as an analog front end (AFE)) 48, a control circuit 102, and a power circuit 103.

As illustrated in FIG. 1, the insulating substrate 21 is electrically coupled with a control substrate 101 through a flexible print substrate 71. The flexible print substrate 71 is provided with the AFE 48. The control substrate 101 is provided with the control circuit 102 and the power circuit 103. The control circuit 102 is, for example, a field programmable gate array (FPGA). The control circuit 102 controls detection operation of the sensor unit 10 by supplying control signals to the sensor unit 10, the gate line drive circuit 15, and the signal line selection circuit 16. The power circuit 103 supplies a voltage signal such as a power source signal SVS (refer to FIG. 4) to the sensor unit 10 and the gate line drive circuit 15.

As illustrated in FIG. 1, the insulating substrate 21 includes a detection region AA and a peripheral region GA. The detection region AA is a region overlapping a plurality of photodiodes PD (refer to FIG. 4) included in the sensor unit 10. The peripheral region GA is a region outside the detection region AA and not overlapping the photodiodes PD. The gate line drive circuit 15 and the signal line selection circuit 16 are provided in the peripheral region GA.

As illustrated in FIG. 2, the fingerprint detection apparatus 1 further includes a detection controller 11 and a detector 40. Some or all of functions of the detection controller 11 are included in the control circuit 102. Some or all of functions of the detector 40 except for the AFE 48 are included in the control circuit 102.

The sensor unit 10 is an optical sensor including the photodiodes PD as photoelectric conversion elements. Each photodiode PD included in the sensor unit 10 outputs an electric signal in accordance with light incident on the photodiode PD to the signal line selection circuit 16 as a detection signal Vdet. The sensor unit 10 performs detection in accordance with a gate drive signal VGCL supplied from the gate line drive circuit 15.

The detection controller 11 is a circuit configured to supply a control signal to each of the gate line drive circuit 15, the signal line selection circuit 16, and the detector 40 and control their operations. The detection controller 11 supplies various kinds of control signals such as a start signal STV, a clock signal CK, and a reset signal RST1 to the gate line drive circuit 15. The detection controller 11 also supplies various kinds of control signals such as a selection signal SEL to the signal line selection circuit 16.

The gate line drive circuit 15 is a circuit configured to drive a plurality of gate lines GCL (refer to FIG. 3) based on various kinds of control signals. The gate line drive circuit 15 sequentially or simultaneously selects some gate lines GCL and supplies the gate drive signal VGCL to the selected gate lines GCL. Accordingly, the gate line drive circuit 15 selects some photodiodes PD coupled with the gate lines GCL.

Figure 3:
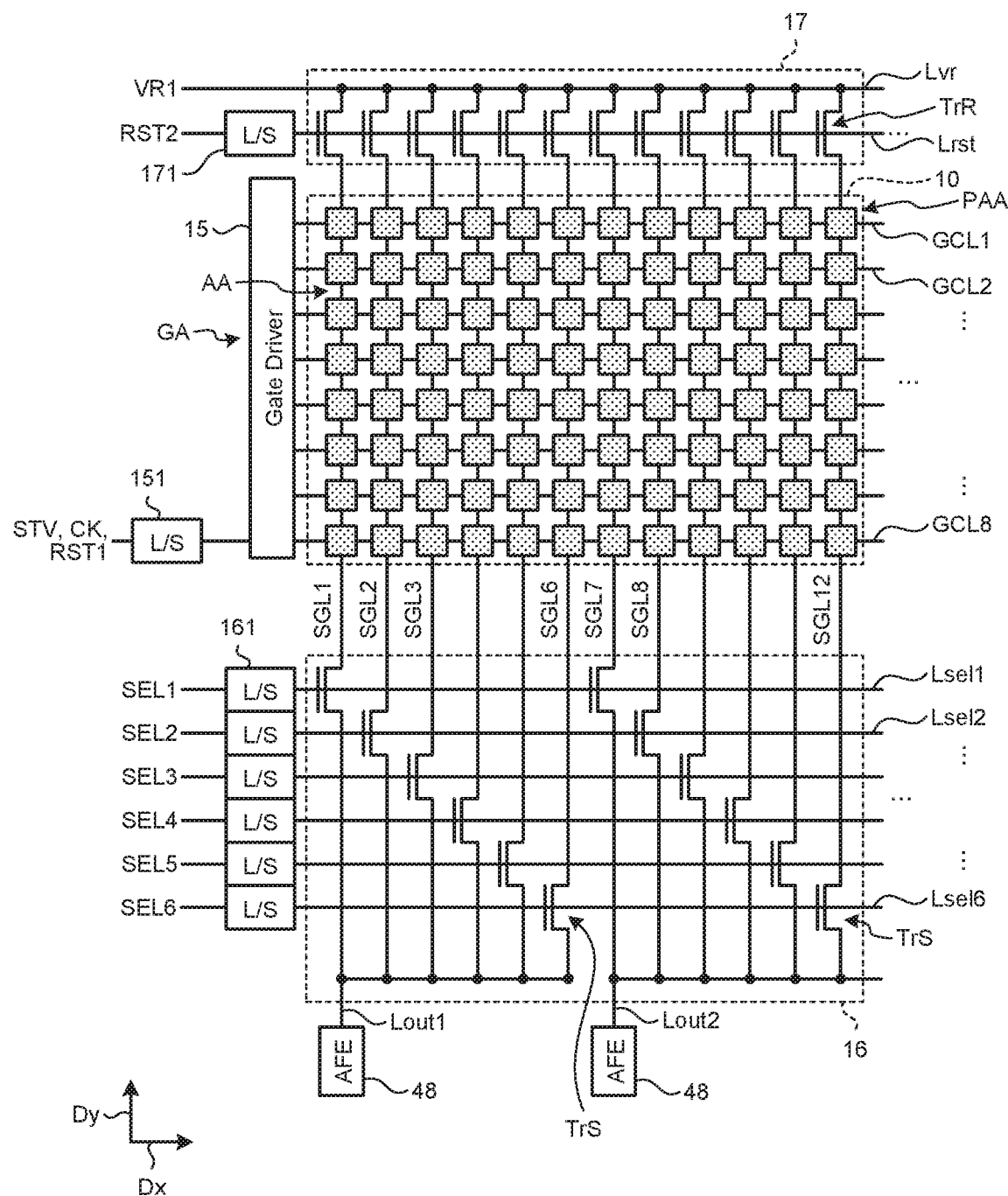
FIG. 3 is a circuit diagram illustrating the fingerprint detection apparatus.

The signal line selection circuit 16 is a switch circuit configured to sequentially or simultaneously select a plurality of signal lines SGL (refer to FIG. 3). The signal line selection circuit 16 couples each selected signal line SGL with the AFE 48 based on the selection signal SEL supplied from the detection controller 11. Accordingly, the signal line selection circuit 16 outputs the detection signal Vdet of each corresponding photodiode PD to the detector 40.

The detector 40 includes the AFE 48, a signal processor 44, a coordinate extractor 45, a storage unit 46, and a detection timing controller 47. The detection timing controller 47 controls the AFE 48, the signal processor 44, and the coordinate extractor 45 to operate in synchronization based on a control signal supplied from the detection controller 11.

The AFE 48 is a signal processing circuit having at least functions of a detection signal amplifier 42 and an A/D converter 43. The detection signal amplifier 42 amplifies the detection signal Vdet. The A/D converter 43 converts an analog signal output from the detection signal amplifier 42, into a digital signal.

The signal processor 44 is a logic circuit configured to detect, based on an output signal from the AFE 48, a predetermined physical quantity input to the sensor unit 10. The signal processor 44 can detect irregularities of the surface of a finger or a palm based on a signal from the AFE 48 when the finger is in contact with or in the proximity of a detection surface.

The storage unit 46 temporarily stores a signal calculated by the signal processor 44. The storage unit 46 may be, for example, a random access memory (RAM) or a register circuit.

The coordinate extractor 45 is a logic circuit configured to calculate detection coordinates of irregularities of the surface of a finger or the like when contact or proximity of the finger is detected by the signal processor 44. The coordinate extractor 45 combines the detection signals Vdet output from the respective photodiodes PD of the sensor unit 10 to generate two-dimensional information indicating the shape of irregularities of the surface of a finger or the like. The coordinate extractor 45 may output each detection signal Vdet as a sensor output Vo without calculating the detection coordinates.

Figure 4:
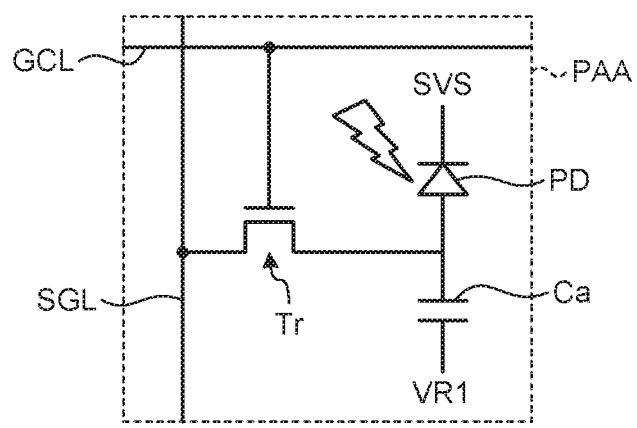
FIG. 4 is a circuit diagram illustrating a partial detection region.
Figure 5:
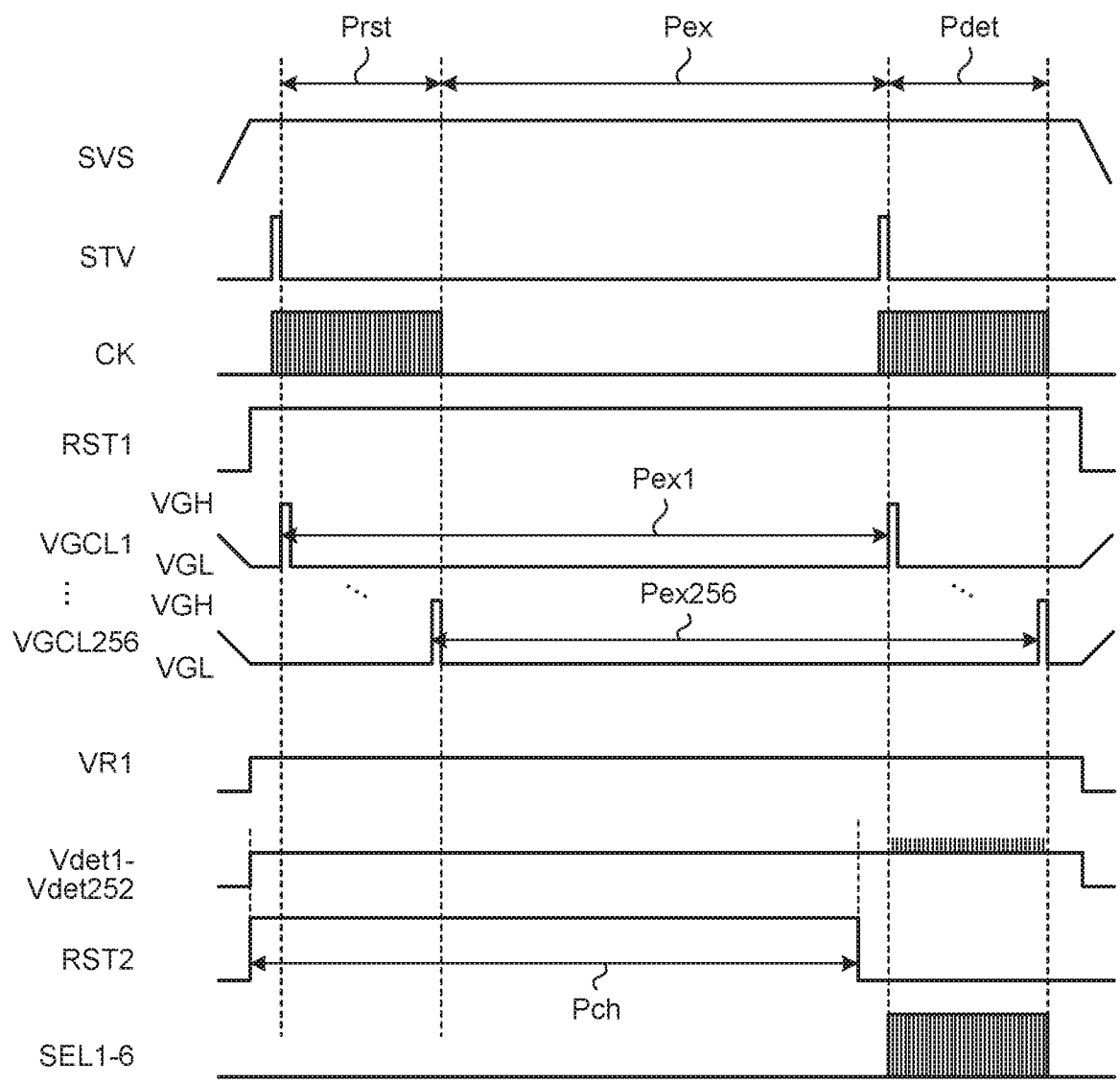
FIG. 5 is a timing waveform diagram illustrating exemplary operations of the fingerprint detection apparatus.

Subsequently, an exemplary circuit configuration and exemplary operations of the fingerprint detection apparatus 1 will be described below. FIG. 3 is a circuit diagram illustrating the fingerprint detection apparatus. FIG. 4 is a circuit diagram illustrating a partial detection region. FIG. 5 is a timing waveform diagram illustrating exemplary operations of the fingerprint detection apparatus.

As illustrated in FIG. 3, the sensor unit 10 includes a plurality of partial detection regions PAA arrayed in a matrix having a row-column configuration. As illustrated in FIG. 4, each partial detection region PAA includes a photodiode PD, a capacitor Ca, and a first switching element Tr. The first switching element Tr is provided for each photodiode PD. The first switching element Tr is achieved by a thin film transistor, and in this example, is achieved by an n-channel metal oxide semiconductor (MOS) thin film transistor (TFT). The gate of the first switching element Tr is coupled with a gate line GCL. The source of the first switching element Tr is coupled with a signal line SGL. The drain of the first switching element Tr is coupled with the anode of the photodiode PD and the capacitor Ca.

The power source signal SVS is supplied from the power circuit 103 to the cathode of the photodiode PD. A reference signal VR1 as the initial potential of the capacitor Ca is supplied from the power circuit 103 to the capacitor Ca.

When the partial detection region PAA is irradiated with light, current in accordance with the quantity of the light flows to the photodiode PD, and accordingly, electric charge is accumulated in the capacitor Ca. When the first switching element Tr is turned on, current flows to the signal line SGL in accordance with the electric charge accumulated in the capacitor Ca. The signal line SGL is coupled with the AFE 48 through the signal line selection circuit 16. Accordingly, the fingerprint detection apparatus 1 can detect, for each partial detection region PAA, a signal in accordance with the quantity of light incident on the photodiode PD.

As illustrated in FIG. 3, each gate line GCL extends in a first direction Dx and is coupled with a plurality of partial detection regions PAA arrayed in the first direction Dx. A plurality of gate lines GCL1, GCL2, . . . , GCL8 are arrayed in a second direction Dy and each coupled with the gate line drive circuit 15. In the following description, the gate lines GCL1, GCL2, ..., GCL8 are simply referred to as gate lines GCL when not needed to be distinguished from each other. The number of gate lines GCL is eight but merely exemplary, and the number of arrayed gate lines GCL may be larger than eight, for example, may be 256.

The first direction Dx is an in-plane direction parallel to the insulating substrate 21, for example, parallel to the gate lines GCL. The second direction Dy is an in-plane direction parallel to the insulating substrate 21 and orthogonal to the first direction Dx. The second direction Dy may intersect the first direction Dx instead of being orthogonal to the first direction Dx.

Each signal line SGL extends in the second direction Dy and is coupled with a plurality of partial detection regions PAA arrayed in the second direction Dy. A plurality of signal lines SGL1, SGL2, ..., SGL12 are arrayed in the first direction Dx and each coupled with the signal line selection circuit 16 and a reset circuit 17. The number of signal lines SGL is twelve but merely exemplary, and the number of arrayed signal lines SGL may be larger than twelve, for example, may be 252. In FIG. 3, the sensor unit 10 is provided between the signal line selection circuit 16 and the reset circuit 17. The signal line selection circuit 16 and the reset circuit 17 are not limited to this configuration but may be coupled with end parts of each signal line SGL in a direction along the signal line SGL.

The gate line drive circuit 15 receives various kinds of control signals such as the start signal STV, the clock signal CK, and a reset signal RST through a level shifter 151. The gate line drive circuit 15 includes a plurality of second switching elements TrG (refer to FIG. 7) and a shift register (not illustrated). The gate line drive circuit 15 sequentially selects the gate lines GCL1, GCL2, ..., GCL8 in a time divisional manner through operation of the shift register and the second switching elements TrG. The gate line drive circuit 15 supplies the gate drive signal VGCL to a plurality of first switching elements Tr through selected gate lines GCL. Accordingly, a plurality of partial detection regions PAA arrayed in the first direction Dx are selected as detection targets.

The signal line selection circuit 16 includes a plurality of selection signal lines Lsel, a plurality of output signal lines Lout, and a plurality of third switching elements TrS. The third switching elements TrS are provided for a plurality of signal lines SGL, respectively. Six signal lines SGL1, SGL2, ..., SGL6 are coupled with a common output signal line Lout1. Six signal lines SGL7, SGL8, ..., SGL12 are coupled with a common output signal line Lout2. The output signal lines Lout1 and Lout2 are each coupled with the AFE 48.

The signal lines SGL1, SGL2, ..., SGL6 are referred to as a first signal line block, and the signal lines SGL7, SGL8, ..., SGL12 are referred to as a second signal line block. A plurality of selection signal lines Lsel are coupled with the gates of third switching elements TrS, respectively, included in each signal line block. Each selection signal line Lsel is coupled with the gates of the third switching elements TrS, respectively, in the signal line blocks. Specifically, the selection signal lines Lsel1, Lsel2, ..., Lsel6 are coupled with the third switching elements TrS corresponding to the signal lines SGL1, SGL2, ..., SGL6, respectively. The selection signal line Lsel1 is coupled with the third switching element TrS corresponding to the signal line SGL1, and the third switching element TrS corresponding to the signal line SGL7. The selection signal line Lsel2 is coupled with the third switching element TrS corresponding to the signal line SGL2, and the third switching element TrS corresponding to the signal line SGL8.

The control circuit 102 (refer to FIG. 1) sequentially supplies the selection signals SEL to the selection signal lines Lsel through a level shifter 161. Accordingly, the signal line selection circuit 16 sequentially selects the signal lines SGL in each signal line block in a time divisional manner through operation of the third switching elements TrS. The signal line selection circuit 16 simultaneously selects signal lines SGL in the respective signal line blocks. With such a configuration, the fingerprint detection apparatus 1 can achieve reduction in the number of integrated circuits (IC) including the AFE 48 or the number of terminals of the ICs.

As illustrated in FIG. 3, the reset circuit 17 includes a reference signal line Lvr, a reset signal line Lrst, and a fourth switching element TrR. The fourth switching element TrR is provided for each signal line SGL. The reference signal line Lvr is coupled with one of the source and drain of each fourth switching element TrR. The reset signal line Lrst is coupled with the gate of each fourth switching element TrR.

The control circuit 102 supplies a reset signal RST2 to the reset signal line Lrst through a level shifter 171. Accordingly, the fourth switching elements TrR are turned on, and the signal lines SGL are electrically coupled with the reference signal line Lvr. The power circuit 103 supplies the reference signal VR1 to the reference signal line Lvr. Accordingly, the reference signal VR1 is supplied to the capacitors Ca included in a plurality of partial detection regions PAA.

As illustrated in FIG. 5, the fingerprint detection apparatus 1 has a reset duration Prst, an exposure duration Pex, and a reading duration Pdet. The power circuit 103 supplies the power source signal SVS to the cathode of each photodiode PD across the reset duration Prst, the exposure duration Pex, and the reading duration Pdet. At a time before the reset duration Prst starts, the control circuit 102 supplies the reference signal VR1 and the reset signal RST2 as high-level voltage signals to the reset circuit 17. The control circuit 102 supplies the start signal STV to the gate line drive circuit 15, which starts the reset duration Prst.

In the reset duration Prst, the shift register included in the gate line drive circuit 15 sequentially selects gate lines GCL, based on the start signal STV, the clock signal CK, and the reset signal RST1. The gate line drive circuit 15 sequentially supplies the gate drive signal VGCL to the gate lines GCL. The gate drive signal VGCL has a waveform in pulses having a high-level voltage VGH and a low-level voltage VGL. In FIG. 5, 256 gate lines GCL are provided, and gate drive signals VGCL1, ..., VGCL256 are sequentially supplied to the respective gate lines GCL.

Accordingly, in the reset duration Prst, the capacitors Ca of all partial detection regions PAA are sequentially electrically coupled with the signal lines SGL and supplied with the reference signal VR1. As a result, the capacitance of each capacitor Ca is reset.

After the gate drive signal VGCL256 is supplied to the corresponding gate line GCL, the exposure duration Pex starts. Actual exposure durations Pex1, ..., Pex256 start and end at timings different among the partial detection regions PAA corresponding to the gate lines GCL. The exposure durations Pex1, ..., Pex256 each start at a timing when the gate drive signal VGCL changes from the high-level voltage VGH to the low-level voltage VGL in the reset duration Prst. The exposure durations Pex1, ..., Pex256 each end at a timing when the gate drive signal VGCL changes from the low-level voltage VGL to the high-level voltage VGH in the reading duration Pdet. The lengths of exposure time of the exposure durations Pex1, . . . , Pex256 are equal.

In each exposure duration Pex, current flows in accordance with light incident on the photodiode PD in each partial detection region PAA. As a result, electric charge is accumulated in each capacitor Ca.

At a timing before the reading duration Pdet starts, the control circuit 102 sets the reset signal RST2 to be the low-level voltage. Accordingly, operation of the reset circuit 17 stops. In the reading duration Pdet, similarly to the reset duration Prst, the gate line drive circuit 15 sequentially supplies the gate drive signals VGCL1, . . . , VGCL256 to the gate lines GCL.

For example, in a duration in which the gate drive signal VGCL1 is at the high-level voltage VGH, the control circuit 102 sequentially supplies selection signals SEL1, . . . , SEL6 to the signal line selection circuit 16. Accordingly, the signal lines SGL of partial detection regions PAA selected by the gate drive signal VGCL1 are sequentially or simultaneously coupled with the AFE 48. As a result, the detection signal Vdet is supplied to the AFE 48. Similarly, in a duration in which each gate drive signal VGCL is at the high-level voltage VGH, the signal line selection circuit 16 sequentially selects signal lines SGL. Accordingly, in the reading duration Pdet, the fingerprint detection apparatus 1 can output the detection signals Vdet of all partial detection regions PAA to the AFE 48.

The fingerprint detection apparatus 1 may perform fingerprint detection by repeatedly executing the reset duration Prst, the exposure duration Pex, and the reading duration Pdet. Alternatively, the fingerprint detection apparatus 1 may start detection operation at a timing when contact or proximity of a finger or the like with the detection surface is detected.

Figure 6:
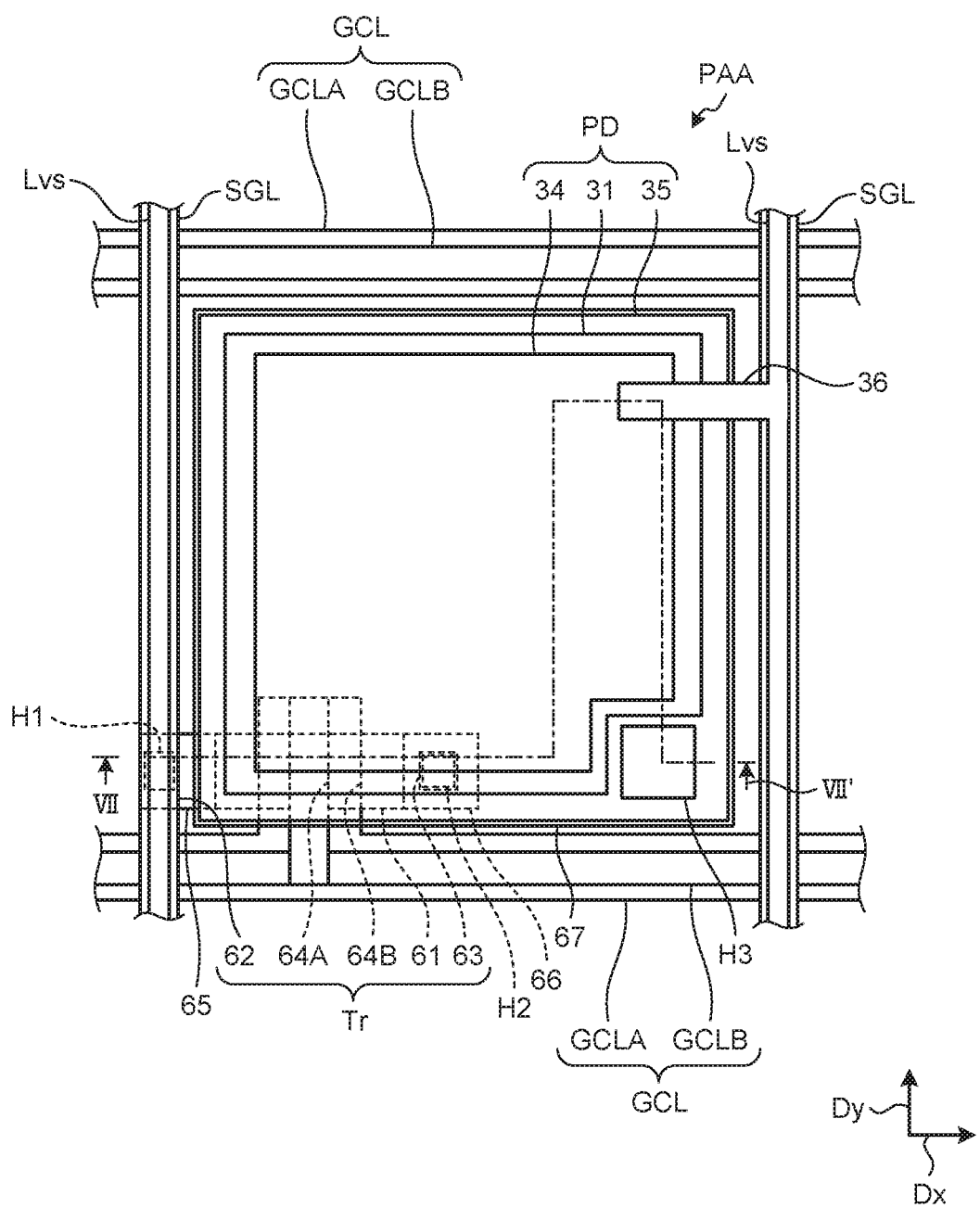
FIG. 6 is a plan view schematically illustrating the partial detection region of the fingerprint detection apparatus according to the first embodiment.
Figure 7:
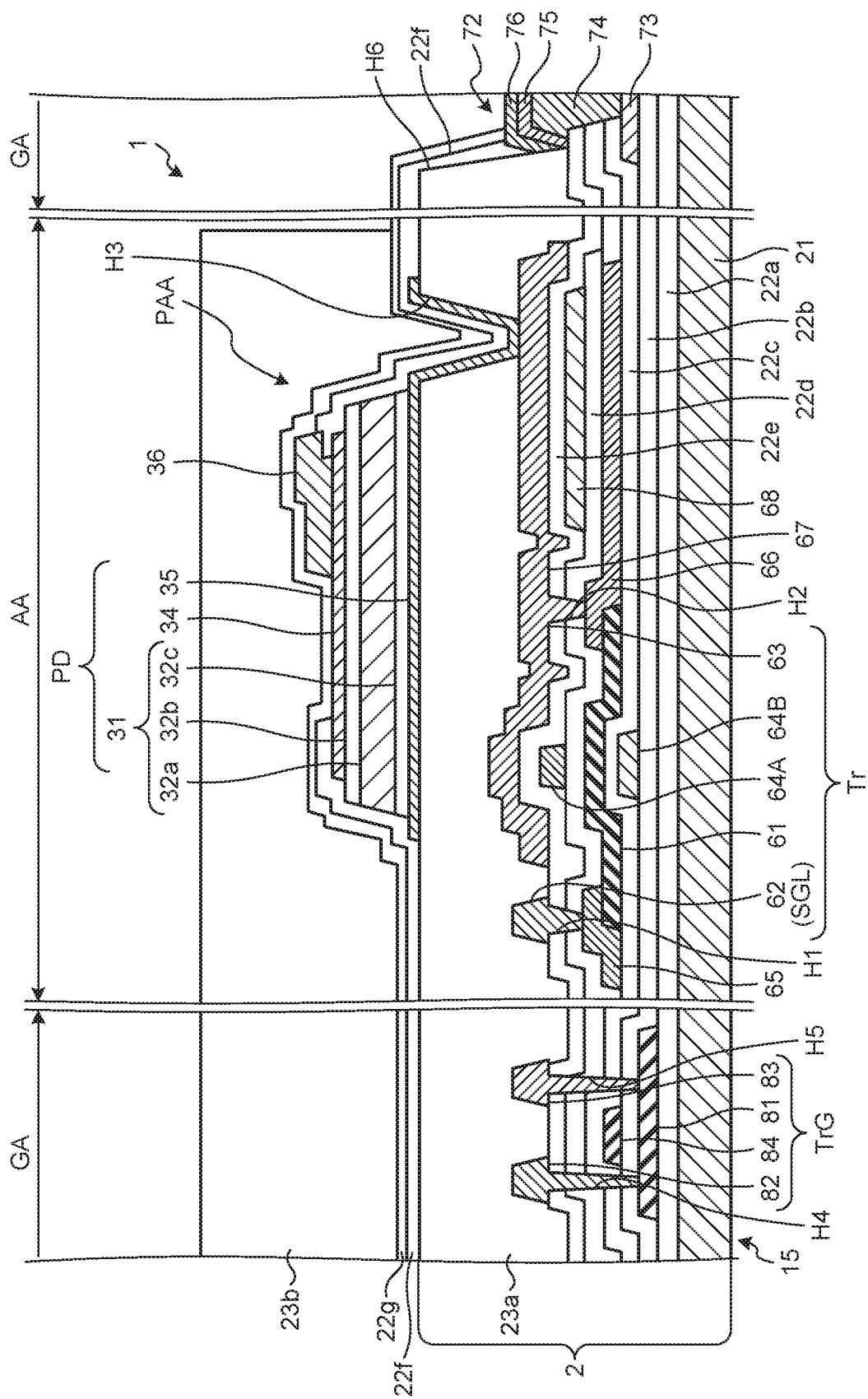
FIG. 7 is a cross-sectional view taken along line VII-VII' in FIG. 6.

Subsequently, a detailed configuration of the fingerprint detection apparatus 1 will be described below. FIG. 6 is a plan view schematically illustrating a partial detection region of the fingerprint detection apparatus according to the first embodiment. FIG. 7 is a cross-sectional view taken along line VII-VII' in FIG. 6. In FIG. 7, to indicate the relation between a layer structure of the detection region AA and a layer structure of the peripheral region GA, a section taken along line VII-VII' and a section of a part including a second switching element TrG in the peripheral region GA are schematically illustrated in connection with each other. In addition, in FIG. 7, a section of a part of the peripheral region GA, which includes a terminal unit 72, is schematically illustrated in connection.

In description of the fingerprint detection apparatus 1, among directions orthogonal to the surface of the insulating substrate 21, the direction from the insulating substrate 21 to the photodiodes PD is defined as an "up direction", and the direction from the photodiodes PD to the insulating substrate 21 is defined as a "down direction". "Plan view" is a view in a direction orthogonal to the surface of the insulating substrate 21.

As illustrated in FIG. 6, a partial detection region PAA is a region surrounded by gate lines GCL and signal lines SGL. In the present embodiment, each gate line GCL includes a first gate line GCLA and a second gate line GCLB. The first gate line GCLA overlaps the second gate line GCLB. The first gate line GCLA and the second gate line GCLB are provided in different layers with insulating layers (a third inorganic insulating layer 22c and a fourth inorganic insulating layer 22d (refer to FIG. 7)) interposed therebetween. The first gate line GCLA and the second gate line GCLB are electrically coupled with each other at an optional place and supplied with gate drive signals VGCL having the same potential. At least one of the first gate line GCLA and the second gate line GCLB is coupled with the gate line drive circuit 15. In FIG. 6, the first gate line GCLA and the second gate line GCLB have widths different from each other but may have the same width.

A photodiode PD is provided in the region surrounded by the gate lines GCL and the signal lines SGL. The photodiode PD includes a third semiconductor 31, an upper electrode 34, and a lower electrode 35. The photodiode PD is, for example, a photodiode of a positive intrinsic negative diode (PIN) type.

Specifically, as illustrated in FIG. 7, in the photodiode PD, the lower electrode 35, the third semiconductor 31, and the upper electrode 34 are stacked in the stated order on a first organic insulating layer 23a of a backplane 2. The backplane 2 is a drive circuit substrate configured to drive a sensor for each predetermined detection region. The backplane 2 includes the insulating substrate 21, the first switching elements Tr, the second switching elements TrG, various wires, and the like provided to the insulating substrate 21.

The third semiconductor 31 is made of amorphous silicon (a-Si). The third semiconductor 31 includes an i-type semiconductor 32a, a p-type semiconductor 32b, and an n-type semiconductor 32c. The i-type semiconductor 32a, the p-type semiconductor 32b, and the n-type semiconductor 32c are specific examples of photoelectric conversion elements. In FIG. 7, the n-type semiconductor 32c, the i-type semiconductor 32a, and the p-type semiconductor 32b are stacked in the stated order in the direction orthogonal to the surface of the insulating substrate 21. However, the n-type semiconductor 32c, the i-type semiconductor 32a, and the p-type semiconductor 32b may be stacked in the opposite order, i.e., in the stated order of the p-type semiconductor 32b, the i-type semiconductor 32a, and the n-type semiconductor 32c.

The lower electrode 35 is the anode of the photodiode PD and an electrode for reading the detection signal Vdet. The lower electrode 35 is made of a metallic material such as molybdenum (Mo) or aluminum (Al). Alternatively, the lower electrode 35 may be a multilayer film of a plurality of layers of these metallic materials. The lower electrode 35 may be made of a translucent conductive material such as indium tin oxide (ITO).

The n-type semiconductor 32c forms an n+ region of a-Si doped with impurities. The p-type semiconductor 32b forms a p+ region of a-Si doped with impurities. The i-type semiconductor 32a is, for example, an undoped intrinsic semiconductor and has conductivity lower than those of the n-type semiconductor 32c and the p-type semiconductor 32b.

The upper electrode 34 is the cathode of the photodiode PD and an electrode for supplying the power source signal SVS to a photoelectric conversion layer. The upper electrode 34 is a translucent conductive layer of ITO or the like and provided for each photodiode PD.

As illustrated in FIG. 7, a sixth inorganic insulating layer 22f and a seventh inorganic insulating layer 22g are provided on the first organic insulating layer 23a. The sixth inorganic insulating layer 22f covers a peripheral part of the upper electrode 34 and is provided with an opening at a position overlapping the upper electrode 34. A coupling wire 36 is coupled with the upper electrode 34 through a part of the upper electrode 34, at which the sixth inorganic insulating layer 22f is not provided. The seventh inorganic insulating layer 22g is provided on the sixth inorganic insulating layer 22f and covers the upper electrode 34 and the coupling wire

36. A second organic insulating layer 23*b* that is a flattening layer is provided on the seventh inorganic insulating layer 22*g*.

As illustrated in FIG. 6, the upper electrode 34 is coupled with a power source signal line Lvs through the coupling wire 36. The power source signal line Lvs is a wire through which the power source signal SVS is supplied to the photodiode PD. In the present embodiment, the power source signal line Lvs overlaps each signal line SGL and extends in the second direction Dy. A plurality of partial detection regions PAA arrayed in the second direction Dy are coupled with the power source signal line Lvs common thereto. With such a configuration, each partial detection region PAA can have an increased opening. The lower electrode 35, the third semiconductor 31, and the upper electrode 34 have rectangular shapes in plan view. However, the shapes of the lower electrode 35, the third semiconductor 31, and the upper electrode 34 are not limited thereto but may be changed as appropriate.

As illustrated in FIG. 6, each first switching element Tr is provided near an intersection of a gate line GCL and a signal line SGL. The first switching element Tr includes a first semiconductor 61, a source electrode 62, a drain electrode 63, a first gate electrode 64A, and a second gate electrode 64B.

The first semiconductor 61 is made of oxide semiconductor. More preferably, the first semiconductor 61 is made of transparent amorphous oxide semiconductor (TAOS) among oxide semiconductors. When such an oxide semiconductor is used in the first switching element Tr, leakage current of the first switching element Tr can be reduced. Specifically, with the first switching element Tr, leakage current from any non-selected partial detection region PAA can be reduced in the reading duration Pdet illustrated in FIG. 5. Accordingly, the fingerprint detection apparatus 1 can have an improved S/N ratio.

The first semiconductor 61 is provided in the first direction Dx and intersects the first gate electrode 64A and the second gate electrode 64B in plan view. The first gate electrode 64A and the second gate electrode 64B are provided as bifurcations of the first gate line GCLA and the second gate line GCLB, respectively. In other words, parts of the first gate line GCLA and the second gate line GCLB, which overlap the first semiconductor 61 functions as the first gate electrode 64A and the second gate electrode 64B, respectively. The first gate electrode 64A and the second gate electrode 64B are made of aluminum (Al), copper (Cu), silver (Ag), molybdenum (Mo), or an alloy of these materials. A channel region is formed at a part of the first semiconductor 61, which overlaps the first gate electrode 64A and the second gate electrode 64B.

One end of the first semiconductor 61 is coupled with the source electrode 62 through a contact hole H1. The other end of the first semiconductor 61 is coupled with the drain electrode 63 through a contact hole H2. A part of the signal line SGL, which overlaps the first semiconductor 61 is the source electrode 62. A part of a third conductive layer 67, which overlaps the first semiconductor 61 functions as the drain electrode 63. The third conductive layer 67 is coupled with the lower electrode 35 through a contact hole H3. With such a configuration, the first switching element Tr can perform switching of coupling and cutoff between the photodiode PD and the signal line SGL.

Subsequently, a layer configuration of the first switching element Tr will be described below. As illustrated in FIG. 7, the first switching element Tr is provided on the insulating substrate 21. The insulating substrate 21 is, for example, a glass substrate. Alternatively, the insulating substrate 21 may be a resin substrate or a resin film made of resin such as polyimide. In the fingerprint detection apparatus 1, the first switching element Tr including an oxide semiconductor is formed on the insulating substrate 21. Thus, the fingerprint detection apparatus 1 can easily obtain an increased area of the detection region AA as compared to a case in which a semiconductor substrate such as a silicon substrate is used.

The second gate electrode 64B is provided on the insulating substrate 21 with a first inorganic insulating layer 22*a* and a second inorganic insulating layer 22*b* interposed therebetween. An inorganic insulating layer such as the first inorganic insulating layer 22*a* or the second inorganic insulating layer 22*b* is achieved by a silicon oxide film (SiO), a silicon nitride film (SiN), a silicon oxynitride film (SiON), or the like. Each inorganic insulating layer is not limited to a single layer but may be a multilayer film.

The third inorganic insulating layer 22*c* is provided on the second inorganic insulating layer 22*b* and covers the second gate electrode 64B. The first semiconductor 61, a first conductive layer 65, and a second conductive layer 66 are provided on the third inorganic insulating layer 22*c*. The first conductive layer 65 is provided to cover an end part of the first semiconductor 61, which is coupled with the source electrode 62. The second conductive layer 66 is provided to cover an end part of the first semiconductor 61, which is coupled with the drain electrode 63.

The fourth inorganic insulating layer 22*d* is provided on the third inorganic insulating layer 22*c* and covers the first semiconductor 61, the first conductive layer 65, and the second conductive layer 66. The first gate electrode 64A is provided on the fourth inorganic insulating layer 22*d*. The first semiconductor 61 is provided between the first gate electrode 64A and the second gate electrode 64B in the direction orthogonal to the insulating substrate 21. Accordingly, the first switching element Tr has what is called a dual gate structure. However, the first switching element Tr may have a top gate structure in which the first gate electrode 64A is provided but the second gate electrode 64B is not provided, or may have a bottom gate structure in which the first gate electrode 64A is not provided but only the second gate electrode 64B is provided.

A fifth inorganic insulating layer 22*e* is provided on the fourth inorganic insulating layer 22*d* and covers the first gate electrode 64A. The source electrode 62 (signal line SGL) and the drain electrode 63 (the third conductive layer 67) are provided on the fifth inorganic insulating layer 22*e*. In the present embodiment, the drain electrode 63 is the third conductive layer 67 provided on the first semiconductor 61 with the fourth inorganic insulating layer 22*d* and the fifth inorganic insulating layer 22*e* interposed therebetween. The fourth inorganic insulating layer 22*d* and the fifth inorganic insulating layer 22*e* are provided with the contact hole H1 and the contact hole H2. The first conductive layer 65 is exposed at a bottom part of the contact hole H1. The source electrode 62 is electrically coupled with the first semiconductor 61 through the contact hole H1 and the first conductive layer 65. Similarly, the second conductive layer 66 is exposed at a bottom part of the contact hole H2. The drain electrode 63 is electrically coupled with the first semiconductor 61 through the contact hole H2 and the second conductive layer 66.

The first conductive layer 65 is provided between the source electrode 62 and the first semiconductor 61 at a part overlapping at least the bottom part of the contact hole H1 and is in contact with the first semiconductor 61. The second conductive layer 66 is provided between the drain electrode 63 and the first semiconductor 61 at a part overlapping at least the bottom part of the contact hole H2 and is in contact with the first semiconductor 61. Since the first conductive layer 65 and the second conductive layer 66 are provided in the fingerprint detection apparatus 1, the first semiconductor 61 can be prevented from being removed by etching solution when the contact holes H1 and H2 are formed by etching. Accordingly, since the first switching elements Tr in the detection region AA and the second switching elements TrG in the peripheral region GA can be formed through the same process, the fingerprint detection apparatus 1 can achieve reduction of manufacturing cost.

The first conductive layer 65, the second conductive layer 66, and the third conductive layer 67 are made of a metallic material such as aluminum (Al), copper (Cu), silver (Ag), or molybdenum (Mo), or an alloy of these materials. The first conductive layer 65 and the second conductive layer 66 may be made of any conductive material that can prevent the progress of etching when the contact holes H1 and H2 are formed.

The third conductive layer 67 is provided in a region overlapping the photodiode PD in plan view. The third conductive layer 67 is also provided above the first semiconductor 61, the first gate electrode 64A, and the second gate electrode 64B. In other words, the third conductive layer 67 is provided between the first gate electrode 64A and the lower electrode 35 in the direction orthogonal to the insulating substrate 21. Accordingly, the third conductive layer 67 functions as a protective layer that protects the first switching element Tr.

The second conductive layer 66 extends oppositely to the third conductive layer 67 in a region not overlapping the first semiconductor 61. In the region not overlapping the first semiconductor 61, a fourth conductive layer 68 is provided on the fourth inorganic insulating layer 22d. The fourth conductive layer 68 is provided between the second conductive layer 66 and the third conductive layer 67. Accordingly, capacitance is generated between the second conductive layer 66 and the fourth conductive layer 68, and capacitance is generated between the third conductive layer 67 and the fourth conductive layer 68. The capacitance generated by the second conductive layer 66, the third conductive layer 67, and the fourth conductive layer 68 is the capacitance of the capacitor Ca illustrated in FIG. 4.

The first organic insulating layer 23a is provided on the fifth inorganic insulating layer 22e and covers the source electrode 62 (signal line SGL) and the drain electrode 63 (third conductive layer 67). The first organic insulating layer 23a is a flattening layer that flattens irregularities formed at the first switching element Tr and various conductive layers. The photodiode PD is provided on the first organic insulating layer 23a. The lower electrode 35 is electrically coupled with the third conductive layer 67 through the contact hole H3 provided to the first organic insulating layer 23a. In other words, the third conductive layer 67 is electrically coupled with the lower electrode 35 as the anode of the photodiode PD and provided between the photodiode PD and the first gate electrode 64A of the first switching element Tr.

The second switching elements TrG of the gate line drive circuit 15 are provided in the peripheral region GA. The second switching elements TrG are provided on the insulating substrate 21 on which the first switching elements Tr are provided. Each second switching element TrG includes a second semiconductor 81, a source electrode 82, a drain electrode 83, and a gate electrode 84.

The second semiconductor 81 is made of polycrystalline silicone. More preferably, the second semiconductor 81 is made of low temperature polycrystalline silicone (hereinafter referred to as LTPS). The second switching element TrG including the LTPS can be manufactured at a process temperature of 600° C. or higher. Thus, circuits such as the gate line drive circuit 15 and the signal line selection circuit 16 can be formed on the substrate on which the first switching elements Tr are provided. Polycrystalline silicone has a carrier mobility higher than that of a-Si. Thus, in the fingerprint detection apparatus 1, since the second switching elements TrG are made of polycrystalline silicone, the size of the gate line drive circuit 15 can be reduced. As a result, in the fingerprint detection apparatus 1, the area of the peripheral region GA can be reduced. The second switching elements TrG made of polycrystalline silicone are more reliable than those made of a-Si.

The second semiconductor 81 is provided on the first inorganic insulating layer 22a. Thus, the first semiconductor 61 of each first switching element Tr is provided at a position further separated from the insulating substrate 21 than the second semiconductor 81 of each second switching element TrG in the direction orthogonal to the insulating substrate 21. Accordingly, the second semiconductor 81 made of polycrystalline silicone and the first semiconductor 61 made of oxide semiconductor can be formed on the same insulating substrate 21.

The gate electrode 84 is provided above the second semiconductor 81 with the second inorganic insulating layer 22b interposed therebetween. The gate electrode 84 is provided in a layer in which the second gate electrode 64B is provided. The second switching element TrG has what is called a top gate structure. However, the second switching element TrG may have a dual gate structure or a bottom gate structure.

The source electrode 82 and the drain electrode 83 are provided on the fifth inorganic insulating layer 22e. The source electrode 82 and the drain electrode 83 are provided in a layer in which the source electrode 62 and the drain electrode 63 of the first switching element Tr are provided. Contact holes H4 and H5 are provided through the second inorganic insulating layer 22b to the fifth inorganic insulating layer 22e. The source electrode 82 is electrically coupled with the second semiconductor 81 through the contact hole H4. The drain electrode 83 is electrically coupled with the second semiconductor 81 through the contact hole H5.

The contact holes H4 and H5 are formed through four inorganic insulating layers (the second inorganic insulating layer 22b to the fifth inorganic insulating layer 22e), and the contact holes H1 and H2 are formed through two inorganic insulating layers (the fourth inorganic insulating layer 22d and the fifth inorganic insulating layer 22e). Accordingly, the lengths of the contact holes H4 and H5 in the direction orthogonal to the insulating substrate 21 are longer than those of the contact holes H1 and H2. In this case as well, since the first switching element Tr includes the first conductive layer 65 and the second conductive layer 66, the contact holes H1 and H2 and the contact holes H4 and H5 can be formed through the same process in the fingerprint detection apparatus 1.

The third switching elements TrS included in the signal line selection circuit 16, which are illustrated in FIG. 3, may have configurations same as those of the second switching elements TrG. Specifically, a semiconductor of each third switching element TrS is made of polycrystalline silicone, more preferably, LTPS. In this case, the fingerprint detection apparatus 1 can have a reduced circuit size of the signal line selection circuit 16. The semiconductor of each third switching element TrS is not limited thereto but may be made of oxide semiconductor such as TAOS. Similarly, the fourth switching elements TrR included in the reset circuit 17, which are illustrated in FIG. 3, may have configurations same as those of the second switching elements TrG. Specifically, a semiconductor of each fourth switching element TrR is made of polycrystalline silicone, more preferably, LTPS. In this case, the fingerprint detection apparatus 1 can have a reduced circuit size of the reset circuit 17. The semiconductor of each fourth switching element TrR is not limited thereto but may be made of oxide semiconductor such as TAOS.

The terminal unit 72 is provided at a position different from a region in which the gate line drive circuit 15 is provided in the peripheral region GA. The terminal unit 72 includes a first terminal conductive layer 73, a second terminal conductive layer 74, a third terminal conductive layer 75, and a fourth terminal conductive layer 76. The first terminal conductive layer 73 is provided in a layer in which the second gate electrode 64B is provided on the second inorganic insulating layer 22b. A contact hole H6 is provided through the third inorganic insulating layer 22c, the fourth inorganic insulating layer 22d, the fifth inorganic insulating layer 22e, and a first organic insulating layer 23.

The second terminal conductive layer 74, the third terminal conductive layer 75, and the fourth terminal conductive layer 76 are stacked in the stated order in the contact hole H6 and electrically coupled with the first terminal conductive layer 73. The second terminal conductive layer 74 can be formed through a process same as that of the third conductive layer 67 or the like by using a material same as that of the third conductive layer 67 or the like. The third terminal conductive layer 75 can be formed through a process same as that of the lower electrode 35 by using a material same as that of the lower electrode 35. The fourth terminal conductive layer 76 can be formed through a process same as those of the coupling wire 36 and the power source signal line Lvs (refer to FIG. 6) by using a material same as those of the coupling wire 36 and the power source signal line Lvs.

Although FIG. 7 illustrates one terminal unit 72, a plurality of terminal units 72 are arrayed at intervals. Each terminal unit 72 is electrically coupled with the flexible print substrate 71 (refer to FIG. 1) through, for example, an anisotropic conductive film (ACF).

As described above, the fingerprint detection apparatus 1 of the present embodiment includes: the insulating substrate 21; a plurality of photoelectric conversion elements (photodiodes PD) arrayed in the detection region AA of the insulating substrate 21 and each configured to output a signal in accordance with light incident on the photoelectric conversion element; a first switching element Tr provided for each photoelectric conversion element and including the first semiconductor 61 made of oxide semiconductor; the gate lines GCL coupled with the first switching elements Tr and extending in the first direction Dx; the signal lines SGL coupled with the first switching elements Tr and extending in the second direction Dy intersecting the first direction Dx; and the gate line drive circuit 15 including a second switching element TrG that includes the second semiconductor 81 made of polycrystalline silicone, the gate line drive circuit 15 being provided in the peripheral region GA outside the detection region AA and configured to drive the gate lines GCL.

With this configuration, in the fingerprint detection apparatus 1, the first switching elements Tr including the oxide semiconductor are formed on the insulating substrate 21. Thus, the fingerprint detection apparatus 1 can easily obtain an increased area of the detection region AA as compared to a case in which a semiconductor substrate such as a silicon substrate is used. The first switching elements Tr provided to the photoelectric conversion elements as the photodiodes PD include the first semiconductor made of oxide semiconductor and can reduce leakage current. Accordingly, the fingerprint detection apparatus 1 can have an improved SN ratio. Each second switching element TrG in the peripheral region includes the second semiconductor 81 made of polycrystalline silicone and has a high carrier mobility. Thus, the circuit size of the gate line drive circuit 15 can be reduced. As a result, the area of the peripheral region GA can be reduced. In addition, since the gate line drive circuit 15 is provided to the insulating substrate 21, the circuit size of ICs included in the control circuit 102 can be reduced.

Second Embodiment

Figure 8:
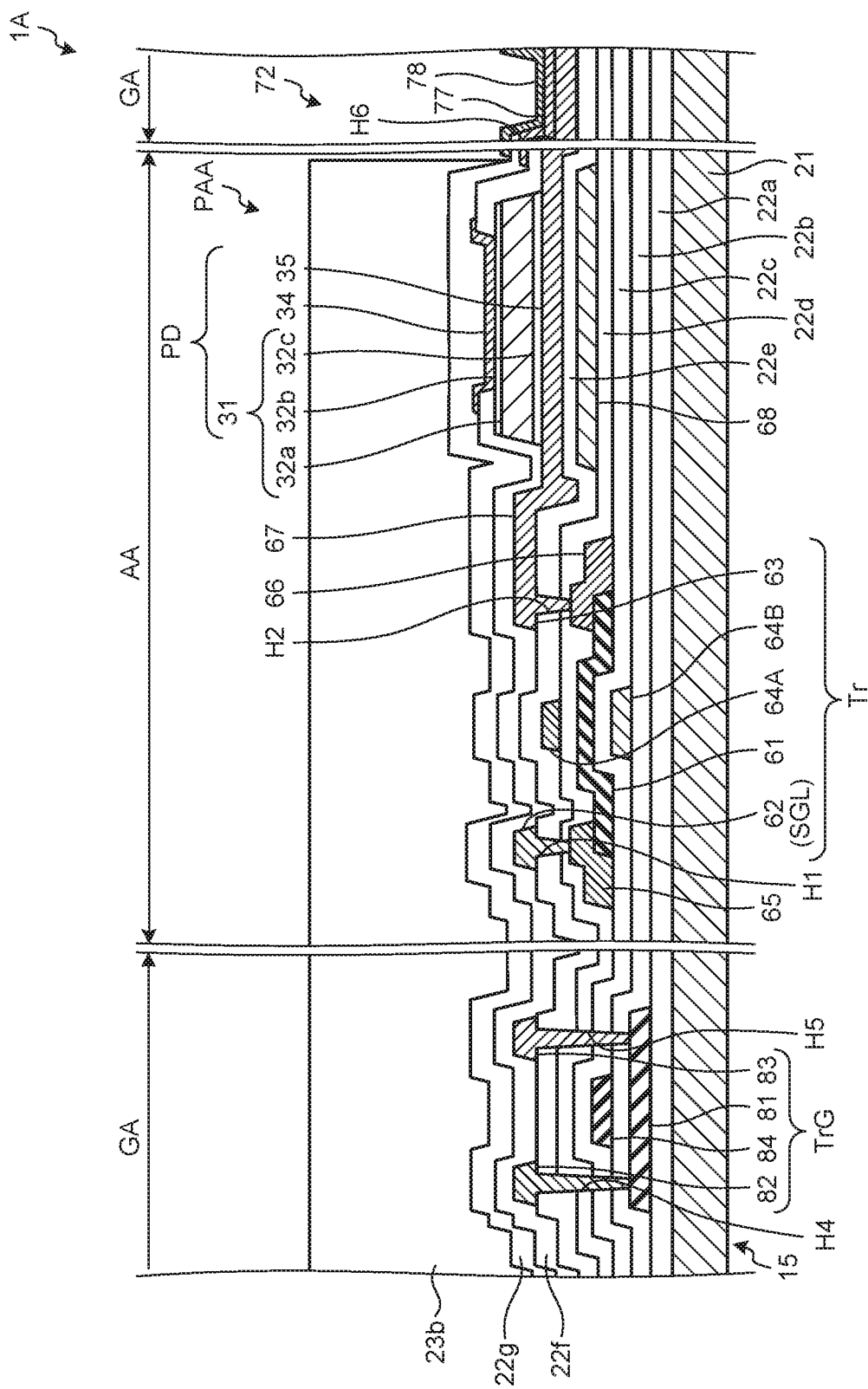
FIG. 8 is a cross-sectional view illustrating a schematic section configuration of a fingerprint detection apparatus according to a second embodiment.

FIG. 8 is a cross-sectional view illustrating a schematic section configuration of a fingerprint detection apparatus according to a second embodiment. As illustrated in FIG. 8, in this fingerprint detection apparatus 1A of the present embodiment, the configurations of the first switching elements Tr and the second switching elements TrG are same as those in the first embodiment. The drain electrode 63 is the third conductive layer 67 provided on the first semiconductor 61 with the fourth inorganic insulating layer 22d and the fifth inorganic insulating layer 22e interposed therebetween. The third conductive layer 67 serves as the lower electrode 35 that is the anode of the photodiode PD. A part of the third conductive layer 67, which overlaps the third semiconductor 31 is the lower electrode 35, and a part thereof, which overlaps the first semiconductor 61 is the drain electrode 63.

Each photodiode PD is provided on the fifth inorganic insulating layer 22e. The sixth inorganic insulating layer 22f is provided on the fifth inorganic insulating layer 22e and covers the source electrode 62 (signal line SGL) and the drain electrode 63 (third conductive layer 67). The sixth inorganic insulating layer 22f is provided to also cover the source electrode 82 and the drain electrode 83 of each second switching element TrG. The sixth inorganic insulating layer 22f covers a peripheral part of the third semiconductor 31 and is provided with an opening at a position overlapping the third semiconductor 31.

The upper electrode 34 is coupled with the third semiconductor 31 through a part of the third semiconductor 31, at which the sixth inorganic insulating layer 22f is not provided. The seventh inorganic insulating layer 22g is provided to cover the sixth inorganic insulating layer 22f and the upper electrode 34. The second organic insulating layer 23b that is a flattening layer is provided on the seventh inorganic insulating layer 22g. Thus, in the present embodiment, the first organic insulating layer 23a illustrated in FIG. 7 can be omitted to reduce the thickness of the fingerprint detection apparatus 1A.

The upper electrode 34 is made of translucent ITO and thus may be provided across a plurality of partial detection regions PAA. The upper electrode 34 may be continuously provided on the third semiconductor 31 and the sixth inorganic insulating layer 22f to couple a plurality of third semiconductors 31.

The terminal unit 72 includes a fifth terminal conductive layer 77 and a sixth terminal conductive layer 78. The contact hole H6 is provided through the sixth inorganic insulating layer 22f and the seventh inorganic insulating layer 22g. The fifth terminal conductive layer 77 and the sixth terminal conductive layer 78 are provided along the inner wall of the contact hole H6 and a bottom part thereof. The third conductive layer 67 extends to the peripheral region GA and is coupled with the sixth inorganic insulating layer 22f at the bottom part of the contact hole H6. The sixth inorganic insulating layer 22f and the seventh inorganic insulating layer 22g are made of, for example, translucent ITO. The sixth inorganic insulating layer 22f can be formed through a process same as that of the upper electrode 34.

In the present embodiment, each photodiode PD is provided in a region not overlapping the corresponding first switching element Tr. The third conductive layer 67 is provided at a position not overlapping the first gate electrode 64A. The second conductive layer 66 is provided at a position not overlapping the photodiode PD and the fourth conductive layer 68 and covers an end part of the first semiconductor 61. In this case, capacitance generated between the third conductive layer 67 and the fourth conductive layer 68 is the capacitance of the capacitor Ca illustrated in FIG. 3.

Modification of Second Embodiment

Figure 9:
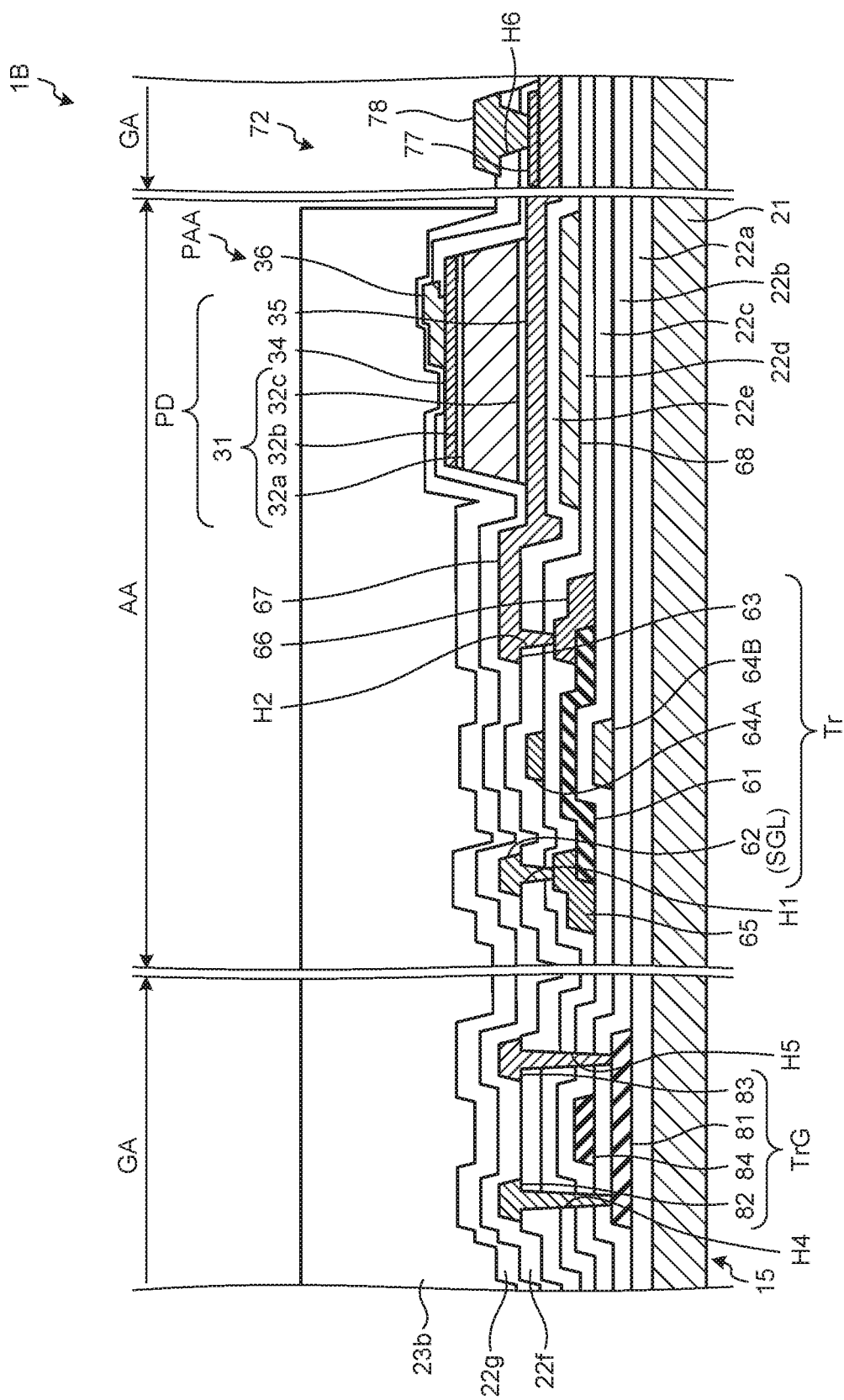
FIG. 9 is a cross-sectional view illustrating a schematic section configuration of a fingerprint detection apparatus according to a modification of the second embodiment.

FIG. 9 is a cross-sectional view illustrating a schematic section configuration of a fingerprint detection apparatus according to a modification of the second embodiment. As illustrated in FIG. 9, this fingerprint detection apparatus 1B of the present modification is different from the fingerprint detection apparatus 1A illustrated in FIG. 8 in that the coupling wire 36 is provided on the upper electrode 34. In the present modification, the upper electrode 34 is provided for each partial detection region PAA. The upper electrode 34 is coupled with the power source signal line Lvs (refer to FIG. 6) through the coupling wire 36.

In the terminal unit 72, the sixth terminal conductive layer 78 is provided on the seventh inorganic insulating layer 22g and coupled with the fifth terminal conductive layer 77 through the contact hole H6.

Third Embodiment

Figure 10:
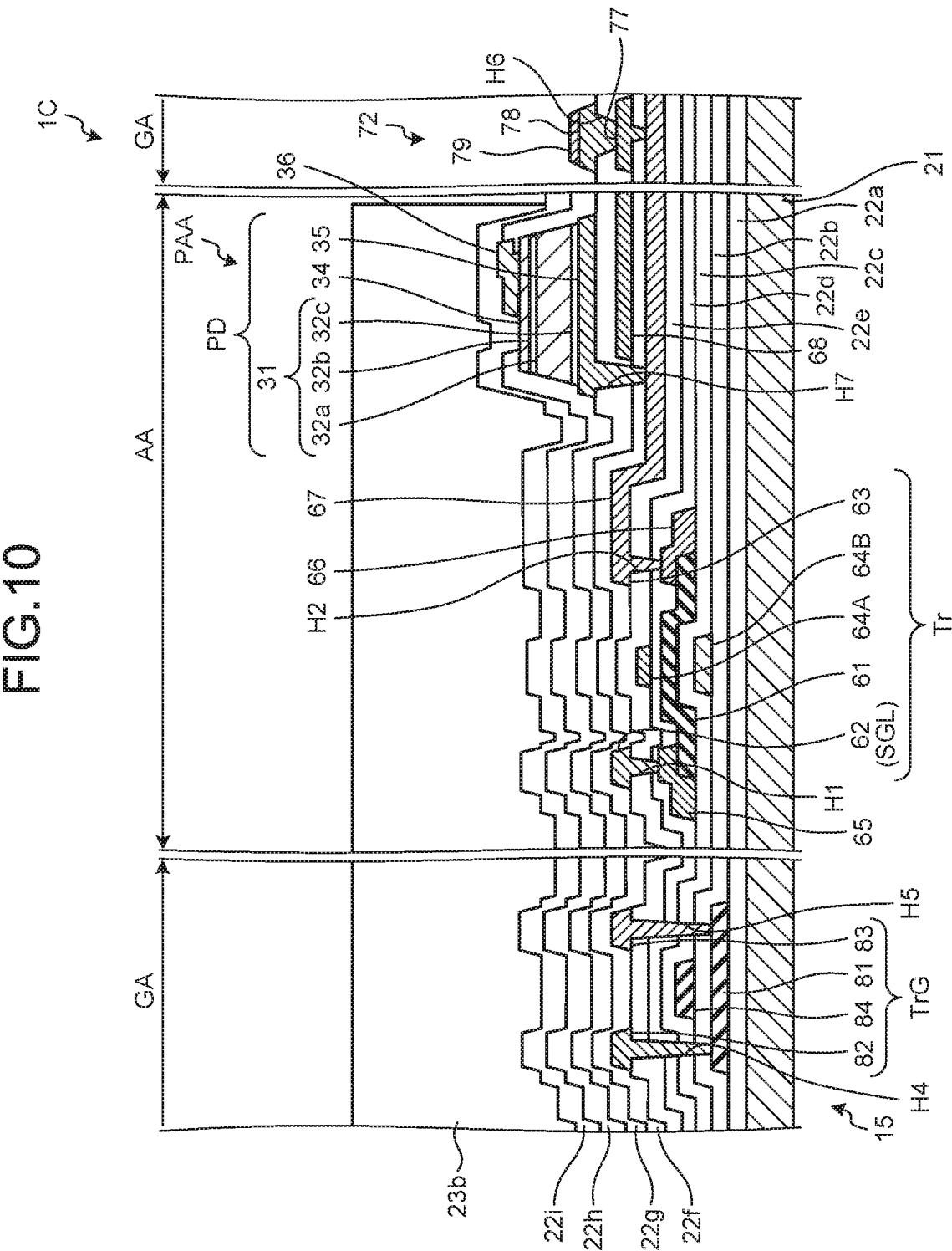
FIG. 10 is a cross-sectional view illustrating a schematic section configuration of a fingerprint detection apparatus according to a third embodiment.

FIG. 10 is a cross-sectional view illustrating a schematic section configuration of a fingerprint detection apparatus according to a third embodiment. As illustrated in FIG. 10, in this fingerprint detection apparatus 1C of the present embodiment, the sixth inorganic insulating layer 22f and the seventh inorganic insulating layer 22g are provided to cover the first switching elements Tr and the second switching elements TrG. The photodiodes PD are provided on the seventh inorganic insulating layer 22g. An eighth inorganic insulating layer 22h and a ninth inorganic insulating layer 22i are provided on the seventh inorganic insulating layer 22g and cover the photodiodes PD.

A contact hole H7 is provided through the sixth inorganic insulating layer 22f and the seventh inorganic insulating layer 22g. The lower electrode 35 of each photodiode PD is electrically coupled with the third conductive layer 67 through the corresponding contact hole H7.

The fourth conductive layer 68 is provided on the sixth inorganic insulating layer 22f in a region overlapping each photodiode PD. The fourth conductive layer 68 is provided between the lower electrode 35 and the third conductive layer 67. Accordingly, capacitance is generated between the lower electrode 35 and the fourth conductive layer 68, and capacitance is generated between the third conductive layer 67 and the fourth conductive layer 68.

The fifth terminal conductive layer 77 of the terminal unit 72 is provided in a layer in which the fourth conductive layer 68 is provided, and is made of a metallic material same as that of the fourth conductive layer 68. The sixth terminal conductive layer 78 is provided in a layer in which the lower electrode 35 is provided, and is made of a metallic material same as that of the lower electrode 35. A seventh terminal conductive layer 79 is provided on the sixth terminal conductive layer 78. The seventh terminal conductive layer 79 is made of, for example, translucent ITO.

Fourth Embodiment

Figure 11:
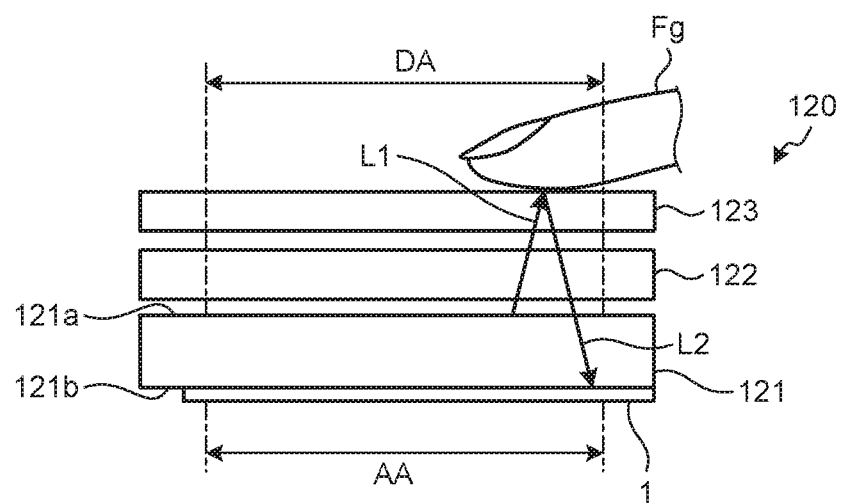
FIG. 11 is a cross-sectional view illustrating a schematic section configuration of a display apparatus according to a fourth embodiment.

FIG. 11 is a cross-sectional view illustrating a schematic section configuration of a display apparatus according to a fourth embodiment. As illustrated in FIG. 11, this display apparatus 120 includes the fingerprint detection apparatus 1, a display panel 121, a touch panel 122, and a cover glass 123. The display panel 121 may be, for example, an organic light emitting diode (organic EL display panel or OLED) or an inorganic EL display (μ-LED or mini-LED) including a light emitting element as a display element. Alternatively, a display panel 20 may be a liquid crystal display (LCD) panel including a liquid crystal element as the display element, or an electrophoretic display (EPD) panel including an electrophoretic element as the display element. The photoelectric conversion elements included in the fingerprint detection apparatus 1 may be an organic material or the like, instead of an amorphous silicon material.

The display panel 121 has a first principal surface 121a, and a second principal surface 121b opposite to the first principal surface 121a. The first principal surface 121a is a surface from which light L1 from the display element is emitted toward the cover glass 123 to display an image. The first principal surface 121a has a display region DA in which an image is displayed.

The touch panel 122 detects a finger Fg in contact with or near the surface of the cover glass 123 by, for example, a capacitive scheme. The touch panel 122 is translucent and can transmit the light L1 and light L2 that is reflected at the interface between the cover glass 123 and air. The display apparatus 120 does not necessarily include the touch panel 122. The display panel 121 may be integrated with the touch panel 122 and have functions of the touch panel 122.

The cover glass 123 is a member for protecting the display panel 121 and the like and covers the display panel 121 and the like. The cover glass 123 is, for example, a glass substrate. Not only the cover glass 123 but also a resin substrate or the like may be provided on the touch panel 122.

The fingerprint detection apparatus 1 is provided opposite to the second principal surface 121b of the display panel 121. The fingerprint detection apparatus 1 can detect irregularities of the surface of the finger Fg by detecting the light L2 reflected at the interface between the cover glass 123 and air. Since the area of the fingerprint detection apparatus 1 can be easily increased, the detection region AA of the fingerprint detection apparatus 1 is provided opposite to the entire display region DA of the display panel 121. The detection region AA is not limited to this configuration but may be provided opposite to a part of the display region DA of the display panel 121.

The fingerprint detection apparatus 1 described in the first to fourth embodiments and the modification is not limited to fingerprint detection but is also applicable to detection of other information related to a living body. The fingerprint detection apparatus 1 is also applicable to, for example, a detection device configured to detect a blood vessel image (vein pattern) of the finger Fg or a palm, the pulse wave, the pulse beat, the blood oxygen level, and the like.

Preferable embodiments of the present disclosure are described above, but the present disclosure is not limited to such embodiments. Contents disclosed in the embodiments are merely exemplary, and various kinds of modifications are possible without departing from the gist of the present disclosure. Any modification performed as appropriate without departing from the gist of the present disclosure belongs to the technical scope of the present disclosure.

What is claimed is:

1. A fingerprint detection apparatus comprising:
an insulating substrate;
a plurality of photodiodes arrayed in a detection region of the insulating substrate, each of the photodiodes configured to output a signal in accordance with light incident on each of the photodiodes;
first switching elements, each corresponding to each of the photodiodes and including a first semiconductor made of oxide semiconductor;
a plurality of gate lines coupled with the first switching elements and extending in a first direction;
a plurality of signal lines coupled with the first switching elements and extending in a second direction intersecting the first direction; and
a gate line drive circuit including a second switching element that includes a second semiconductor made of polycrystalline silicone, the gate line drive circuit being provided in a peripheral region outside the detection region and configured to drive the gate lines,
wherein a distance between the first semiconductor and the insulating substrate is larger than a distance between the second semiconductor and the insulating substrate in a direction orthogonal to a main surface of the insulating substrate.

2. The fingerprint detection apparatus according to claim 1, further comprising a signal line selection circuit configured to sequentially select each signal line and couple the signal line with an analog front-end circuit, wherein the signal line selection circuit includes a third switching element including a semiconductor made of polycrystalline silicone.

3. The fingerprint detection apparatus according to claim 1, wherein
each of the first switching elements includes a source electrode and a drain electrode,
the source electrode is provided above the first semiconductor with an insulating layer interposed therebetween and electrically coupled with the first semiconductor through a first contact hole provided to the insulating layer, and
a first conductive layer provided in a region overlapping at least a bottom part of the first contact hole and in contact with the first semiconductor is provided between the first semiconductor and the source electrode.

4. The fingerprint detection apparatus according to claim 3, wherein
the drain electrode is provided above the first semiconductor with the insulating layer interposed therebetween and electrically coupled with the first semiconductor through a second contact hole provided to the insulating layer, and
a second conductive layer provided in a region overlapping at least a bottom part of the second contact hole and in contact with the first semiconductor is provided between the first semiconductor and the drain electrode.

5. The fingerprint detection apparatus according to claim 4, wherein
the drain electrode is a third conductive layer provided above the first semiconductor, and
the third conductive layer is electrically coupled with an anode of one of the photodiodes and provided between the one of photodiodes and a gate electrode of corresponding one of the first switching elements in a direction orthogonal to a main surface of the insulating substrate.

6. The fingerprint detection apparatus according to claim 1, further comprising a flattening layer covering the first switching elements and the second switching element, wherein the photodiodes are provided on the flattening layer.

7. The fingerprint detection apparatus according to claim 1, wherein
a drain electrode of each of the first switching elements is a third conductive layer provided above the first semiconductor, and
the third conductive layer serves as an anode of corresponding one of the photodiodes.

8. The fingerprint detection apparatus according to claim 1, further comprising an inorganic insulating layer covering the first switching elements and the second switching element, wherein the photodiodes are provided on the inorganic insulating layer.

9. The fingerprint detection apparatus according to claim 8, wherein
a drain electrode of each of the first switching elements is a third conductive layer provided above the first semiconductor, and
an anode of corresponding one of the photodiodes is electrically coupled with the third conductive layer through a contact hole provided to the inorganic insulating layer.

10. The fingerprint detection apparatus according to claim 1, wherein
each of the photodiodes includes a translucent conductive layer that is a cathode, and
the translucent conductive layer is electrically coupled with a common power source signal line through coupling wires.

11. The fingerprint detection apparatus according to claim 10, wherein the common power source signal line overlaps one of the signal lines in plan view.

12. The fingerprint detection apparatus according to claim 1, wherein partial detection regions including corresponding one of the respective photodiodes and corresponding one of the first switching elements are provided in a matrix having a row-column configuration in the detection region.

13. A display apparatus comprising:
the fingerprint detection apparatus according to claim 1; and
a display panel including a display element for displaying an image and disposed opposite to the fingerprint detection apparatus.

14. A fingerprint detection apparatus comprising:
an insulating substrate;
a plurality of photodiodes arrayed in a detection region of the insulating substrate, each of the photodiodes configured to output a signal in accordance with light incident on each of the photodiodes;
first switching elements, each corresponding to each of the photodiodes and including a first semiconductor made of oxide semiconductor;
a plurality of gate lines coupled with the first switching elements and extending in a first direction;

a plurality of signal lines coupled with the first switching elements and extending in a second direction intersecting the first direction; and a gate line drive circuit including a second switching element that includes a second semiconductor made of polycrystalline silicone, the gate line drive circuit being provided in a peripheral region outside the detection region and configured to drive the gate lines, wherein each of the first switching elements includes a source electrode and a drain electrode, the source electrode is provided above the first semiconductor with an insulating layer interposed therebetween and electrically coupled with the first semiconductor through a first contact hole provided to the insulating layer, a first conductive layer provided in a region overlapping at least a bottom part of the first contact hole and in contact with the first semiconductor is provided between the first semiconductor and the source electrode, the drain electrode is provided above the first semiconductor with the insulating layer interposed therebetween and electrically coupled with the first semiconductor through a second contact hole provided to the insulating layer, a second conductive layer provided in a region overlapping at least a bottom part of the second contact hole and in contact with the first semiconductor is provided between the first semiconductor and the drain electrode, the drain electrode is a third conductive layer provided above the first semiconductor, the third conductive layer is electrically coupled with an anode of one of the photodiodes and provided between the one of photodiodes and a gate electrode of corresponding one of the first switching elements in a direction orthogonal to a main surface of the insulating substrate, a fourth conductive layer is provided between the second conductive layer and the third conductive layer, capacitance is generated between the second conductive layer and the fourth conductive layer, and capacitance is generated between the third conductive layer and the fourth conductive layer.

15. The fingerprint detection apparatus according to claim 14, further comprising a signal line selection circuit configured to sequentially select each signal line and couple the signal line with an analog front-end circuit, wherein the signal line selection circuit includes a third switching element including a semiconductor made of polycrystalline silicone.

16. The fingerprint detection apparatus according to claim 14, wherein a distance between the first semiconductor and the insulating substrate is larger than a distance between the second semiconductor and the insulating substrate in a direction orthogonal to a main surface of the insulating substrate.

17. The fingerprint detection apparatus according to claim 14, further comprising a flattening layer covering the first switching elements and the second switching element, wherein the photodiodes are provided on the flattening layer.

18. A fingerprint detection apparatus comprising:

an insulating substrate;

a plurality of photodiodes arrayed in a detection region of the insulating substrate, each of the photodiodes configured to output a signal in accordance with light incident on each of the photodiodes;

first switching elements, each corresponding to each of the photodiodes and including a first semiconductor made of oxide semiconductor;

a plurality of gate lines coupled with the first switching elements and extending in a first direction;

a plurality of signal lines coupled with the first switching elements and extending in a second direction intersecting the first direction;

a gate line drive circuit including a second switching element that includes a second semiconductor made of polycrystalline silicone, the gate line drive circuit being provided in a peripheral region outside the detection region and configured to drive the gate lines; and an inorganic insulating layer covering the first switching elements and the second switching element, wherein the photodiodes are provided on the inorganic insulating layer, a drain electrode of each of the first switching elements is a third conductive layer provided above the first semiconductor, an anode of corresponding one of the photodiodes is electrically coupled with the third conductive layer through a contact hole provided to the inorganic insulating layer, and a fourth conductive layer is provided between the third conductive layer and the anode.

19. The fingerprint detection apparatus according to claim 18, further comprising a signal line selection circuit configured to sequentially select each signal line and couple the signal line with an analog front-end circuit, wherein the signal line selection circuit includes a third switching element including a semiconductor made of polycrystalline silicone.

20. The fingerprint detection apparatus according to claim 18, wherein a distance between the first semiconductor and the insulating substrate is larger than a distance between the second semiconductor and the insulating substrate in a direction orthogonal to a main surface of the insulating substrate.

* * * * *